(12) United States Patent
Baumann et al.

(10) Patent No.: US 12,419,609 B2
(45) Date of Patent: Sep. 23, 2025

(54) REPLACEABLE ATTACHMENT FOR AN ULTRASOUND PROBE

(71) Applicant: Compremium AG, Muri b. Bern (CH)

(72) Inventors: Ulrich André Baumann, Münsingen (CH); Vincent Boris Baumann, Gümligen (CH); Peter Nuot Frei, Dulliken (CH)

(73) Assignee: COMPREMIUM AG, Muri b. Bern (CH)

( * ) Notice: Subject to any disclaimer, the term of this patent is extended or adjusted under 35 U.S.C. 154(b) by 353 days.

(21) Appl. No.: 17/902,034

(22) Filed: Sep. 2, 2022

(65) Prior Publication Data

US 2023/0063412 A1 Mar. 2, 2023

(30) Foreign Application Priority Data

Sep. 2, 2021 (CH) .................................. 70231/2021

(51) Int. Cl.
A61B 8/00 (2006.01)
(52) U.S. Cl.
CPC .......... A61B 8/4461 (2013.01); A61B 8/4281 (2013.01)
(58) Field of Classification Search
None
See application file for complete search history.

(56) References Cited

U.S. PATENT DOCUMENTS

| 5,997,481 | A | 12/1999 | Adams et al. | |
| 6,132,378 | A | 10/2000 | Marino | |
| 2010/0234733 | A1 | 9/2010 | Wahlheim | |
| 2011/0087105 | A1 | 4/2011 | Ridley et al. | |
| 2014/0163382 | A1 | 6/2014 | Gubbini et al. | |
| 2015/0359520 | A1* | 12/2015 | Shan | A61B 8/0858 600/443 |
| 2016/0331344 | A1* | 11/2016 | Hadzic | A61B 8/085 |
| 2017/0128042 | A1* | 5/2017 | Desai | A61B 8/4281 |
| 2017/0209116 | A1* | 7/2017 | Erkamp | A61B 90/92 |
| 2017/0322071 | A1* | 11/2017 | Schmid | A61B 5/7203 |
| 2020/0383660 | A1 | 12/2020 | Rothberg et al. | |

FOREIGN PATENT DOCUMENTS

WO 2016126257 A1 8/2016
WO 2019147940 A1 8/2019

OTHER PUBLICATIONS

Search Report issued on Jan. 20, 2023, in corresponding European Application No. 22192009.3, 15 pages.

* cited by examiner

Primary Examiner — Shahdeep Mohammed
(74) Attorney, Agent, or Firm — Maier & Maier, PLLC

(57) ABSTRACT

A replaceable attachment for an ultrasound probe includes a ring-like fastening region for fastening the attachment to the ultrasound probe, and a flexible membrane arranged on the fastening region. A first liquid or gel-like contact medium is applied to an inner contact surface of the membrane. The contact surface makes contact with an end face of the ultrasound probe when an attachment is fastened to the ultrasound probe. Before the attachment is fastened, the first contact medium is distributed on the contact surface in such a manner that, in an array region of the contact surface, a quantity of the first contact medium per surface is at least twice as large as in a remaining region of the contact surface. A positioning and extent of the array region is adapted to a positioning and extent of a piezo array of the ultrasound probe.

15 Claims, 3 Drawing Sheets

REPLACEABLE ATTACHMENT FOR AN ULTRASOUND PROBE

FIELD

The invention relates to a replaceable attachment for an ultrasound probe with a ring-like fastening region for fastening the attachment to the ultrasound probe, and with a flexible membrane arranged on the fastening region. A first liquid or gel-like contact medium is applied to an inner contact surface of the membrane, the contact surface making contact with an end face of the ultrasound probe when an attachment is fastened to the ultrasound probe. The invention furthermore relates to a packaged attachment for an ultrasound probe and to an ultrasound probe with an attachment.

BACKGROUND

Sonography is well established as an imaging method for investigating organic tissue in medicine and veterinary medicine. Use is conventionally made of an ultrasound probe which is guided over the body surface. The probe comprises an ultrasound head for generating ultrasonic waves, for example by means of a piezo array. They are coupled into the human or animal body via an end face of the ultrasound head. The reflected signals are in turn detected by the ultrasound probe and, on the basis of the duration of the reflected signals, the depths of the reflecting tissue structures can be determined. Image data can then be prepared therefrom, with the brightness of the image information being determined on the basis of the echo signals.

To ensure that the ultrasonic waves are coupled into the body, use is conventionally made of a contact medium, e.g. a hydrogel, which is applied to the end face of the ultrasound probe (or to the skin).

This ultrasound probe is used successively for investigating a plurality of patients. It therefore has to be ensured that no germs are transmitted from one patient to another via the ultrasound probe. This is conventionally undertaken by disinfecting the ultrasound probe between the investigations, with suitable disinfectants generally being applied manually, by means of a sponge or a cloth; in certain cases, dipping into the disinfectant is also possible. The degree of disinfection is generally coordinated with the planned use, i.e., for example, the interaction with intact skin, the interaction with mucus membranes, or the intra-operative or laparoscopic use. In addition, sterile contact media are used. Sterilization by heat is not possible because of the sensitivity of the components of the ultrasound probe.

The disinfection process is relatively time-consuming and, if not carried out correctly or in a manner adapted to the investigation, cannot eliminate the risk of transmitting germs. It is therefore known from the prior art to provide the ultrasound head or the end face thereof with a replaceable sterile attachment which is replaced between consecutive investigations of various patients (single-use or single-patient use).

For example, US 2010/0234733 A1 (P. Wahlheim) discloses a sterile tubular cover, in the closed end region of which a compartment containing a contact medium is provided. If the cover is pulled onto the ultrasound probe, the compartment tears open and releases the contact medium.

A similar cover is disclosed in U.S. Pat. No. 5,997,481 (Ultra Sound Probe Covers, LLC). In this document, the compartment is formed by a flexible membrane which has an opening so that the contact gel can flow into the intermediate space between the membrane and the end face of the ultrasound head.

However, the handling of the covers which cover the entire ultrasound probe and sometimes even the cable which is connected thereto is complicated. In addition, a relatively large quantity of contact medium is in each case necessary and which can also be distributed substantially freely in the region of the ultrasound head. A consistently good signal quality therefore cannot be ensured.

WO 2019/147940 A1 (Butterfly Network, Inc.) describes an attachment for an ultrasound probe, which comprises a vessel for a contact gel which has openings between the vessel and the side facing the ultrasound head and/or the outer side. The contact gel is therefore distributed over the contact surface between the attachment and the end face of the ultrasound head and/or over the contact surface between the attachment and the body surface and thereby assists the transmission of the ultrasonic waves.

However, the vessel causes two additional boundary surfaces which basically impair the ultrasonic signal and the reflected signals. The perforated structure may also be disadvantageous in this respect. In addition, the vessel has to contain a relatively large amount of gel so that sufficient wetting of the contact surfaces is ensured, and this in turn impairs the signal quality.

SUMMARY

It is the object of the invention to provide an attachment which belongs to the technical field mentioned at the beginning and which is simple to handle and permits high signal quality.

According to the invention, before the attachment is fastened, the first contact medium is distributed over the contact surface in such a manner that, in an array region of the contact surface, a quantity of the first contact medium per surface is at least twice as large as in a remaining region of the contact surface. A positioning and extent of the array region is adapted here to a positioning and extent of a piezo array of the ultrasound probe.

The attachment is intended in particular for single use or for exclusive use for one patient, during one treatment sequence (single-patient use), i.e. it is removed from the ultrasound probe after the measurement has been taken or the treatment sequence has ended or before changing to another patient.

The fastening region serves in particular for the encircling fastening to the ultrasound probe, wherein the interacting fastening means of the attachment and of the probe can interact with one another over the entire extent or in regions. The fastening region can be formed with a certain dimensional stability on a ring-like frame, or it is formed, for example, by a section of greater wall thickness formed integrally with the membrane. Said section can have a high degree of flexibility. The geometry of the frame or of the section may be, for example, in the shape of a circular ring, elliptical, regularly or irregularly polygonal, optionally with rounded corner regions.

The fastening means are designed in such a manner that they create a closed space between the membrane of the attachment and the ultrasound probe. Various fastening means can be used within the scope of the invention, e.g. clip geometries, interacting threads, geometries for creating a bayonet connection, magnetic elements, releasable adhesive connections or a press fit which is produced, for example, if the annular fastening region is formed from an elastic material and the latter is stretched as it is being pulled onto a mating section of the ultrasound probe.

The flexible membrane is fastened in particular in an encircling manner to the fastening region. In particular before the attachment is placed on, said membrane is arranged unstretched and also without creases and folds on the fastening region. The free region of the membrane, i.e. the region which is accessible on both main surfaces when the membrane is arranged on the fastening region, is preferably circular. In the case of an isotropic membrane material, a uniform isotropic distribution of the forces acting on the membrane thus results.

The membrane is designed in such a manner that, when the attachment is mounted on the ultrasound probe, the membrane fits as well as possible onto the end face of the ultrasound probe. The membrane preferably has a thickness of 0.01-0.5 mm, preferably 0.025-0.2 mm, particularly preferably 0.035-0.065 mm. Thinner membranes are preferred insofar as they have a minimal influence on the image quality and permit particularly great flexibility, which is in particular of advantage whenever the ultrasound probe has a pressure sensor in order to measure compressive forces in action (via the membrane). Suitable materials for the membrane are silicone or nitrile rubber (NBR), for example. The Shore hardness of the material is 50 Shore A or less, in particular 30 Shore A or less.

The "contact surface" is understood here as meaning exclusively that region of the membrane which is in contact with the end surface of the ultrasound probe when the attachment is fastened. The contact surface can be flat before the attachment is placed thereon and, after it is placed thereon, is deformed in accordance with the geometry of the end surface of the ultrasound probe. The end surface refers here to that surface of the ultrasound probe which, during an investigation of a patient, interacts with the body surface of the patient via the membrane and via which the ultrasonic waves and the reflected signals are decoupled or coupled. The contact surface corresponds in particular substantially to the entire free region of the membrane, i.e. the membrane interacts exclusively with the end surface of the ultrasound probe.

The first contact medium ensures that ultrasound information is reliably transmitted between the membrane and the ultrasound probe. Ideally, the first contact medium is gel-like with a viscosity which prevents the quantity applied in the array region from prematurely flowing away. The substance for the first contact medium is also advantageously selected in such a manner that the membrane can slide on the end face of the ultrasound probe and creasing is avoided.

In particular, the first contact medium is distributed uniformly in the array region, i.e. a first thickness of the layer formed by the first contact medium is substantially constant there. In a remaining region of the contact surface, a second thickness of the first contact medium is accordingly at most half the size of the first thickness. The quantity ratio between the array region and the remaining region before the attachment is mounted on the ultrasound probe is preferably at least 4:1, particularly preferably at least 8:1.

The fact that the array region is adapted to the piezo array of the ultrasound probe can mean that a surface, shape and position of the array region correspond to the surface, shape and positioning of the piezo array. However, the surface of the array region may also be somewhat larger than that of the piezo array in order to ensure that the entire array region is covered by the first contact medium in the assembled state. The surface of the array region may also be somewhat smaller than that of the piezo array if it is assumed that the first contact medium is driven somewhat outwards during the assembly because of the pressure exerted on it. For example, a surface of the array region is at least 60% of the surface of the piezo array and at maximum 175% of the surface of the piezo array. In both cases, it is of advantage if the array region and the surface of the piezo array are mutually centered.

The attachment permits simple and hygienic handling of the ultrasound probe. By means of the precise positioning of the first contact medium on the attachment, the quantity of contact medium between the membrane and the ultrasound head can be reduced. Contact over the full surface is produced in the array region and air bubbles interfering with the imaging are avoided. The overall result is better, more stable and more constant image information. In addition, the solution according to the invention permits simple and safe use, in particular because a manual application of contact medium between the attachment and the ultrasound probe is unnecessary.

Advantageously, the array region is covered substantially over the full area by the first contact medium, and the remaining region of the contact surface is substantially free from contact medium.

The adaptation of the positioning and extent of the array region to the positioning and extent of the piezo array preferably means that the array region is substantially rectangular and the center of the rectangle (i.e. the intersecting point of its diagonal) coincides with the center of the contact surface. Many conventional ultrasound probes comprise a piezo array with a substantially rectangular geometry. A ratio between the width and length of the array is generally at least 1:2. Accordingly, it is advantageous if the array region corresponds to this geometry. "Substantially rectangular" also includes a rectangular shape with rounded corners or an elongate geometry in which the longitudinal and/or transverse sides are slightly concave and/or convex. Advantageously, the ratio between the width and length of the array region corresponds to the ratio between the width and length of the piezo array within the scope of a maximum deviation of ±25%.

Advantageously, a second contact medium is applied to an outer surface of the membrane before the attachment is fastened. The second contact medium ensures that ultrasound information is reliably transmitted between the membrane and the body surface of the patient.

In principle, the second contact medium can be the same composition as the first contact medium. However, the media may also differ from one another. A suitable contact medium is, for example, a water-based gel (hydrogel) with a humectant, a thickening agent and conventional preserving and neutralizing agents. Suitable substances are commercially available, e.g. the product SONOGEL, a sterile ultrasound gel from Sonogel Vertriebs GmbH, Bad Camberg, Germany.

The application of the second contact medium simplifies the management of the medical investigation. Once the attachment is mounted, the probe is immediately ready for operation. It is also ensured that the quantity and the composition of the second contact medium are optimally adapted to the membrane.

Advantageously, the attachment comprises a tamper-evident element having a geometry which is adapted to interact with a contact geometry of the ultrasound probe, when the attachment fastened to the ultrasound probe is being pulled off, in such a manner that the tamper-evident element is mechanically damaged. Accordingly, it can be seen at the attachment whether the latter has already been used once—undesirable multiple uses can therefore be prevented.

The tamper-evident element is in particular a tamper-evident ring. The geometry thereof in particular has predetermined breaking points which are torn open as the ring is being pulled off. The tamper-evident ring may be entirely torn off and may optionally remain on the ultrasound probe. However, it is preferably only partially torn off so that the use which has been carried out is immediately visible, but the tamper-evident ring remains on the attachment. The tamper-evident ring can simultaneously form the fastening region, but it may also be independent of the latter.

The tamper-evident element can also be the flexible membrane of the attachment if the membrane is designed in such a manner that it is damaged when the attachment is pulled off. For this purpose, the membrane can interact with corresponding elements of the ultrasound probe.

However, the tamper-evident element may also be a data store which is destroyed or made unfunctional as it is being pulled off, and therefore it can no longer be subsequently read. In a further variant, the tamper-evident element, after having been pulled off, prevents the building up of a certain preliminary pressure between the membrane and the ultrasound head if the attachment is placed on it again.

The invention also relates to a packaged attachment comprising an attachment according to the invention and a packaging. The packaging has a cup-like main part and a cover. An internal geometry of the cup-like main part is adapted here to an external geometry of the attachment such that the latter can be suitably received in the main part. The cover has an external geometry which is adapted to an internal geometry of the attachment such that the cover can be suitably inserted into the attachment when the attachment is received in the main part.

The attachment is therefore held in a clearly defined position in the packaging. The packaging protects the attachment against contamination and against the first and optionally the second contact medium from drying out.

Advantageously, the packaging is configured in such a manner that the attachment accommodated therein can be arranged on the ultrasound head by the latter being introduced from above into the (opened) packaging, where it grips the attachment and interacts with the fastening means thereof in such a manner that, as the ultrasound head is pulled back out of the packaging, the attachment remains on the ultrasound head, in particular directly in the final placed-on position.

Advantageously, the cover or the main part has a recess on an inner side which runs parallel to the membrane of the attachment when the attachment is received in the packaging, the geometry of which recess is adapted to a geometry of the array region.

The recess therefore creates space for receiving the first contact medium. The recess is preferably formed in the inner side of the cover. In this case, the cover makes contact with the inner side of the membrane and therefore with the contact surface thereof.

Preferably, when the attachment is arranged between the main part and the cover the contact surface of the attachment outside a region defined by the recess is contacted over the full surface in such a manner that an escape of the first contact medium out of the array region into the remaining region is impeded.

The region with full-surface contact completely surrounds the recess, and therefore an escape of the contact medium out of the region defined by the recess is impeded. The region can make contact with the entire contact surface over the full surface outside the array region, or there is just one wall region on the outside adjacent to the array region where the full surface contact takes place. The described geometry preferably leads to the escape of the first contact medium out of the array region being substantially prevented during the maximum storage time for the packaged attachment.

Advantageously, a quantity of the second contact medium is contained in the main part, and therefore the outer surface of the membrane of the received attachment is dipped over a large area in the second contact medium.

This ensures that the ultrasound probe with the attachment mounted thereon is directly ready for use, with the outer surface of the membrane having already been provided with the required contact medium, e.g. contact gel. The outer surface is in particular dipped over the full area in the second contact medium, and therefore, irrespective of the orientation of the packaging, the probe is sufficiently wetted with the second contact medium on its entire end surface formed by the membrane.

The quantity of the second contact medium in the main part can be dimensioned in such a manner that simple rewetting of the attachment is possible. For this purpose, the attachment (attached to the ultrasound probe) is once again introduced into the main part and therefore is entirely or partially dipped once again with the outer surface of the membrane into the second contact medium.

Advantageously, the fastening region of the attachment has a contour for interaction with a mating contour of the ultrasound probe, wherein the contour and the mating contour are designed in such a manner that the attachment can be placed onto the ultrasound probe only in one or two mutually opposite orientations.

The contour and the mating contour can be circumferential contours, protrusions, recesses, etc. The contour can also interact with a mating contour of the packaging, for example to ensure that the orientation of the recess in the cover or in the main part is aligned with the array region. If the array region is axially symmetrical with respect to a diameter of the membrane, a correct alignment is produced both in a first orientation and in an orientation rotated by 180° in relation thereto. When an array region is not correspondingly axially symmetrical, the orientation should be unambiguously determined.

The contour and the mating contour are preferably designed in such a manner that the attachment, as it is being placed onto the ultrasound probe, snaps on the latter in such a manner that said snapping is audible and/or haptically perceivable. The user then immediately knows that the attachment has been completely placed onto the ultrasound probe.

Advantageously, the end face of the ultrasound probe has a convex geometry, and the membrane of the attachment is deformed in accordance with the convex geometry as the attachment is being placed thereon.

The membrane is in particular elastically deformed. The deformation leads in particular to the membrane fitting over a large area onto the end face of the ultrasound probe. The effect achieved by this in combination with the first contact medium and the distribution thereof is that ultrasonic signals can be reliably transmitted between membrane and ultrasound probe.

The attachment according to the invention is suitable in particular for use with an ultrasound head with an integrated pressure sensor. Devices of this type are known, see, for example, CH 707 046 A2 (VeinPress GmbH), WO 2019/106535 A1 (U.A. Baumann, V. Baumann). Corresponding pressure or force information are useful, for example, for determining the veinous pressure or elastic properties of body tissue under investigation. For this purpose, the pressure has to be able to be precisely determined, for example in a measuring range of 5-500, in particular 5-250 mmHg. Minimizing the quantity of the first contact medium between membrane and ultrasound head also contributes to precise pressure measurements.

If the ultrasound head has a pressure sensor, a prestress is advantageously built up in the membrane by the deformation of the membrane, with an initial pressure exerted because of the prestress on the ultrasound probe via the attachment placed thereon being able to be measured with the pressure sensor.

The initial pressure is measured without an additional external force acting on the membrane. The pressure sensor accordingly has a measuring range and a measuring accuracy permitting precise measurement of said initial pressure. With an appropriate measuring range, in addition to the measurement of the prestress, the pressure sensor can generally also be used for measuring a pressure between the ultrasound probe and the body surface during use of the ultrasound probe.

By means of the predefined geometry of the attachment and of the ultrasound probe and the known quantity of contact medium between the membrane and the end surface of the probe, substantially the same situation is produced each time the attachment is placed on, i.e. a desired initial pressure is known.

Very generally, irrespective of the provision according to the invention of the first contact medium, the combination of an ultrasound probe with a replaceable attachment, in which, when the attachment is placed onto the ultrasound probe, a membrane of the attachment is deformed in such a manner that a prestress is built up and that the resulting initial pressure on the ultrasound probe is measured by means of a pressure sensor (force sensor) integrated in the ultrasound probe, is of interest.

A comparison of the measured initial pressure with the desired initial pressure can now be used to calibrate the pressure sensor. This is undertaken with a corresponding calibration device. It can be expedient, for the calibration operation, to predefine an orientation of the ultrasound probe (e.g. vertically downwards) in order to take into consideration gravitational influences. In principle, it is possible to measure the alignment (in particular by means of a position sensor) and either to carry out the calibration only if the alignment is correct or to take the specific orientation mathematically into consideration in the calibration.

The calibration device can be arranged in the ultrasound probe or in an external apparatus connected to the probe. It can be realized by software modules and/or dedicated hardware.

Additionally or alternatively, the measurement of the initial pressure or the comparison with a desired initial pressure may also be used to recognize if the attachment has been correctly placed on, in particular on the basis of a measured initial pressure in a predefined range. The ultrasound probe can be controlled in such a manner that it or a measuring operation is started as soon as an attachment placed on correctly has been recognized.

The corresponding detection device can be arranged in the ultrasound probe or in an external apparatus connected to the probe. It can be realized by software modules and/or dedicated hardware. It can basically also be used irrespective of the provision according to the invention of the first contact medium.

Irrespective of the provision according to the invention of the first contact medium, the pressure sensor can also be calibrated by a first pressure measurement being undertaken in a first spatial orientation of the ultrasound head, while a second pressure measurement is undertaken in a second spatial orientation of the ultrasound head, with an angle of a longitudinal axis of the ultrasound head to the perpendicular between the first spatial orientation and the second spatial orientation differing by at least 45°; in particular, the ultrasound head points substantially vertically downwards in the first spatial orientation and substantially vertically upwards in the second spatial orientation, i.e. the difference in angle is approx. 180°. The weight force, which is directed differently with regard to the ultrasound head, leads to a difference between the first pressure determined in the first pressure measurement and the second pressure determined in the second pressure measurement. This difference can be used for calibrating the pressure sensor, but it can alternatively or additionally also be used to recognize that the attachment is placed on correctly.

The ultrasound head can be provided with a position sensor, and therefore the effective orientation of the head can be precisely determined in the pressure measurements and taken into consideration in the calibration or the detection of the attachment being placed on correctly. In this case, the two orientations can be arbitrary per se if they differ sufficiently in the longitudinal direction with respect to the weight force in action. If the orientation for the two measurements is predefined, a position sensor is not compulsory. In particular, the forces which are in action in the region of a vertical orientation of the ultrasound head (downwards or upwards) only have a low degree of sensitivity to smaller angle errors, i.e. deviations from 0° or 180°.

Apart from for the calibration, the position sensor can basically also be used in the effective pressure measurements in order to take into consideration different influences of the gravitational force in different orientations and to correspondingly correct the identified pressure values.

The calibration device can be arranged in the ultrasound probe or in an external apparatus connected to the probe. It can be realized by software modules and/or dedicated hardware.

In a preferred embodiment, the ultrasound probe comprises a reading device for reading a data store arranged on the placed-on attachment and a blocking device which prevents use of the ultrasound probe with the attachment after expiry of a predetermined period of time.

The data store can be in particular a passive RFID transponder which can be read contactlessly. However, memory or processor chips which communicate wirelessly or interact via contacts on the attachment with mating contacts on the ultrasound probe can also be used.

The predetermined period of time can end at a fixed expiry date, or, when the attachment is used for the first time, a timer is activated which expires after the predetermined period of time.

The blocking device can be arranged in the ultrasound probe or in an external apparatus connected to the probe. It can be realized by software modules and/or dedicated hardware.

Further advantageous embodiments and combinations of features of the invention emerge from the detailed description below and the entirety of the patent claims.

BRIEF DESCRIPTION OF THE DRAWINGS

In the drawings used for explaining the exemplary embodiment.

In principle, identical parts are provided with the same reference signs in the figures.

DETAILED DESCRIPTION

Figure 1:
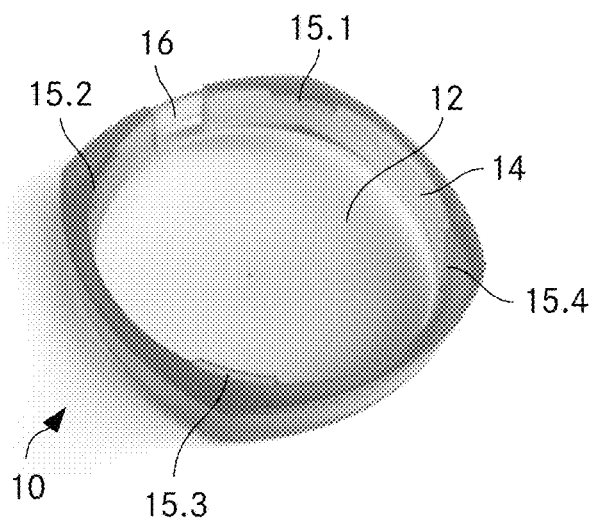
FIG. 1 shows an embodiment of an attachment according to the invention for an ultrasound probe.
Figure 2:
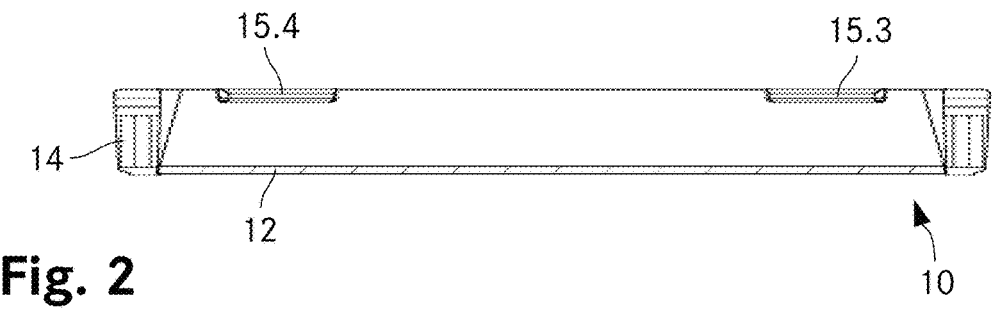
FIG. 2 shows a cross section through the attachment.

FIG. 1 shows an embodiment of an attachment according to the invention for an ultrasound probe, FIG. 2 shows a cross section through the attachment. The attachment 10 is manufactured integrally from silicone with a hardness of 40 Shore A. It comprises a substantially circular membrane 12 with a casing section 14 around it. The casing section is composed of four curved segments of identical length, wherein the radius of curvature of the segments is in each case somewhat larger than the radius of the membrane 12. Accordingly, rounded corners arise at the transitions between adjacent segments. The thickness of the membrane 12 is constantly approx. 0.2 mm, and that of the casing section 14 approx. 0.8 mm. On the side of the casing section 14 opposite the membrane 12, four protrusions 15.1, 15.2, 15.3, 15.4 are formed in the corner regions. They extend radially inwards from the casing section 14. Between two of the protrusions 15.1, 15.2, a rectangular recess 16 is recessed on the inner side of the casing section 14, the recess extending as far as the end of the casing section 14 opposite the membrane 12.

Figure 3:
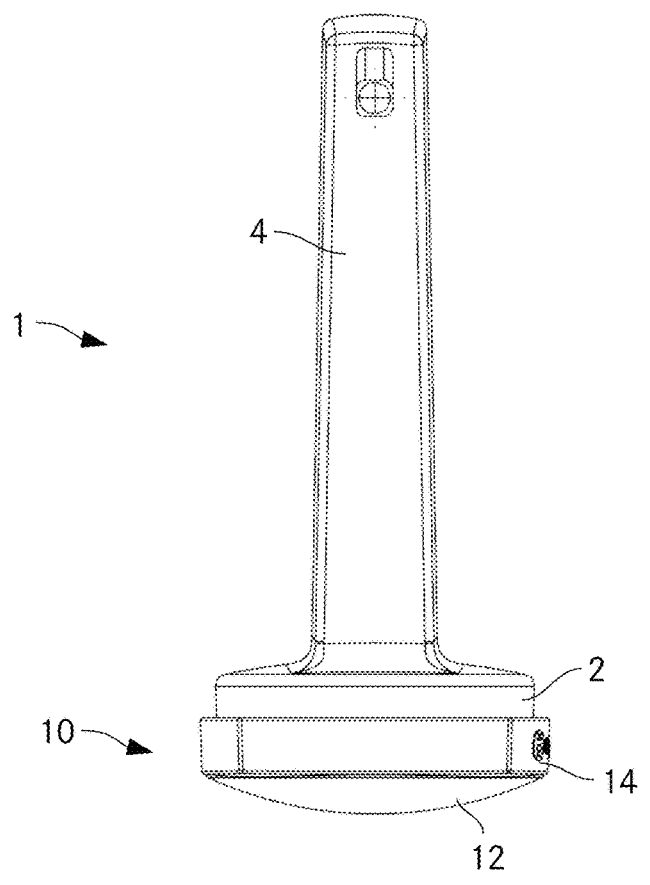
FIG. 3 shows the ultrasound probe with the attachment placed thereon.

FIG. 3 is a side view of the ultrasound probe 1 with an attachment 10 placed thereon. The ultrasound probe 1 comprises the ultrasound head 2 and a handle part 4. The piezo array is accommodated in the ultrasound head. In the example illustrated, a chamber which is closed off at the front by a flexible spherical cap and has a hydraulic medium transparent to ultrasound is arranged in front of the piezo array. The geometry of the spherical cap corresponds in particular to that of a catenoid (i.e. a rotary body of a catenary). The spherical cap is manufactured from a material with a hardness of 40 Shore A, and its elasticity therefore corresponds to that of the membrane 12 of the attachment 10. A pressure measurement probe leads into the chamber, and therefore a pressure exerted on the chamber from the outside via the spherical cap can be measured. The handle part 4 accommodates the further electronic components of the ultrasound probe 1.

The attachment 10 is fastened to the ultrasound probe 1 in the region of the ultrasound head 2. For this purpose, the casing section 14 forms a fastening region, with the protrusions 15.1 . . . 4 interacting with corresponding mating pieces on the ultrasound head 2 in order to hold the attachment 10 axially on the ultrasound probe 1. The internal shape of the casing section 14 itself is adapted to the external shape of the ultrasound head 2, and therefore the attachment 10 is suitably held in the radial direction of the ultrasound probe 1. In addition, the ultrasound head 2 has a protrusion which interacts with the recess 16 in the attachment 10 when the attachment 10 is correctly oriented and prevents mounting the attachment 10 in different orientations, or at least makes this extremely difficult. The protrusion of the head and the recess 16 of the attachment 10 therefore form an anti-rotation lock for the attachment 10. When the attachment 10 is fastened, the membrane 12 fits tightly against the end face, formed by the spherical cap, of the ultrasound head 2 and in particular also takes on the convex shape thereof. The space between the spherical cap and the membrane 12 is sealed peripherally, by interaction of the casing section 14 and the casing surface of the ultrasound head 2.

FIGS. 4A-D are oblique views of elements of a packaging for the attachment, and FIGS. 5A-D show cross sections through the packaging and the attachment. The packaging 50 comprises a container 51 and a cover 61. The container 51 is designed in the manner of a cup and comprises a base 52 and a casing 54 protruding therefrom. The casing 54 is closed off on the side opposite the base 52 by an edge 55 protruding outwards in the manner of a flange. The shape of the container 51 corresponds to the external shape of the casing section of the attachment 10. A gel bath 58 is accommodated in the container 51. Said gel bath is formed by a quantity of sterile ultrasound contact gel which completely covers the base 52.

Figure 4A:
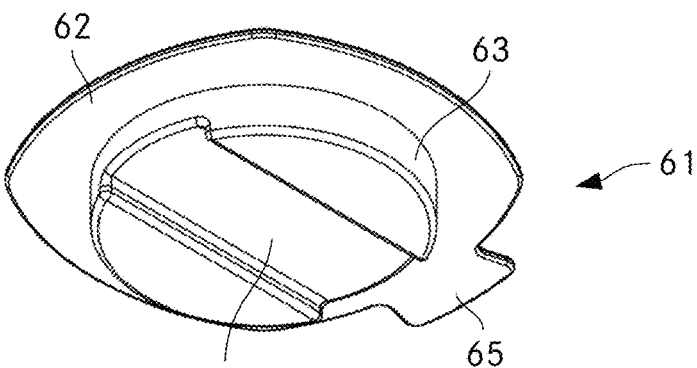
FIG. 4A shows an oblique view of a packaging for the attachment.
Figure 4B:
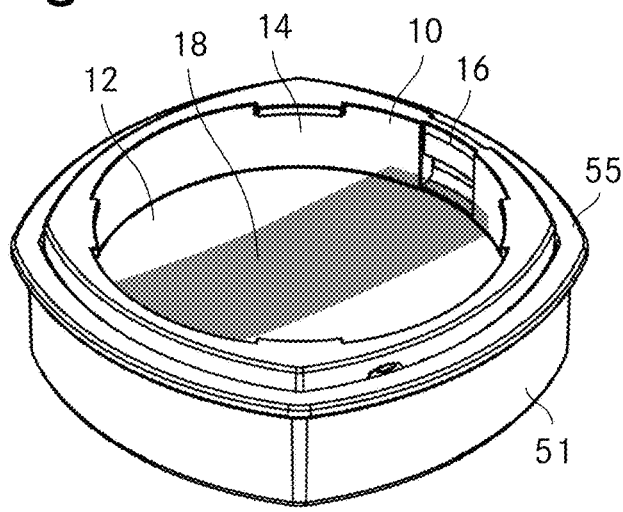
FIG. 4B shows an oblique view of a packaging for the attachment.
Figure 4C:
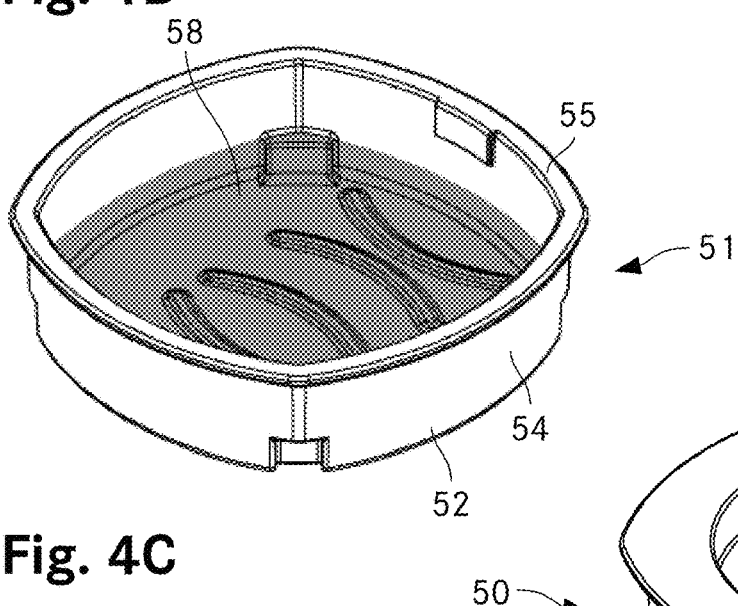
FIG. 4C shows an oblique views of a packaging for the attachment.
Figure 4D:
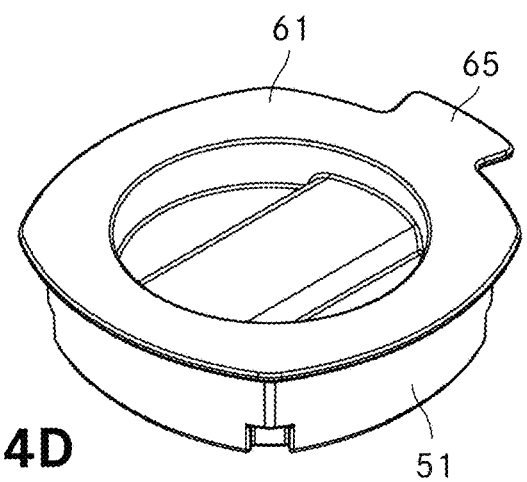
FIG. 4D shows an oblique view of a packaging for the attachment.
Figure 5A:
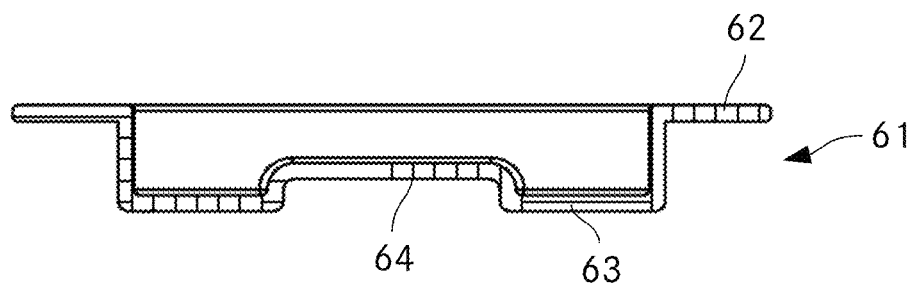
FIG. 5A shows a cross section through the packaging and the attachment.
Figure 5B:
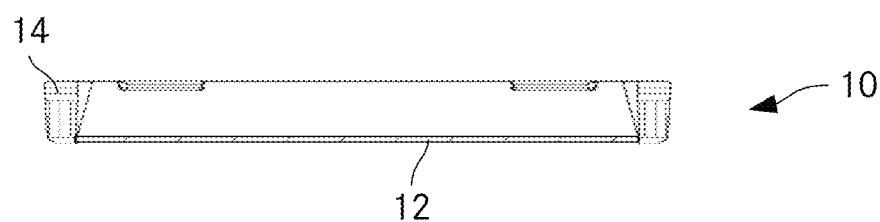
FIG. 5B shows a cross section through the packaging and the attachment
Figure 5C:
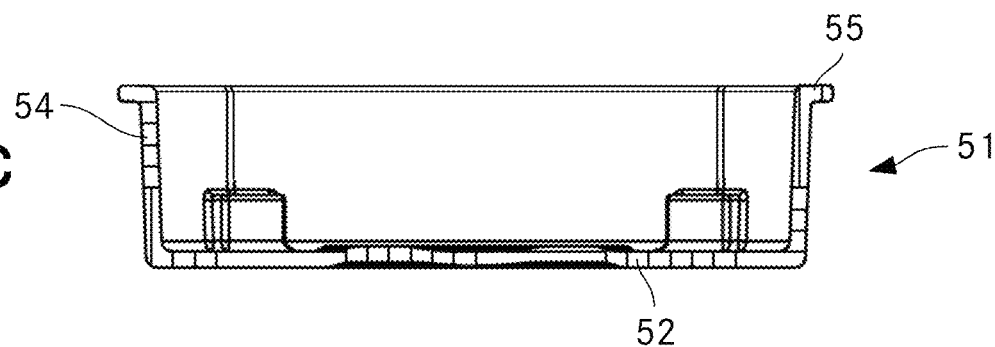
FIG. 5C shows a cross section through the packaging and the attachment
Figure 5D:
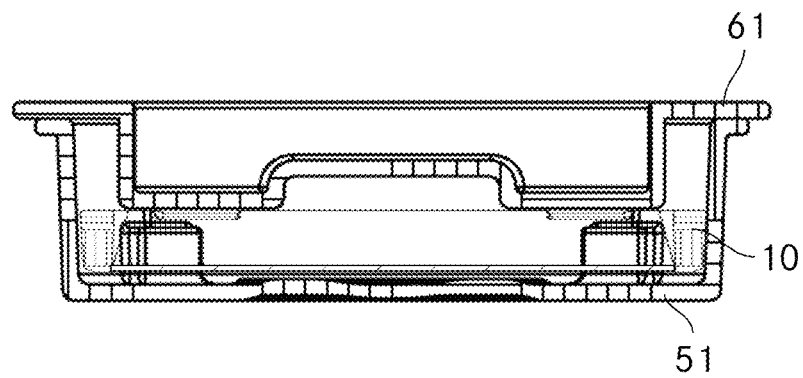
FIG. 5D shows a cross section through the packaging and the attachment.

As shown in FIG. 4B, the attachment 10 can be suitably accommodated in the container 51. The outer side of the membrane 12 is completely wetted here by the gel bath 58. A strip-shaped application 18 with sterile ultrasound contact gel is arranged on the inner side of the membrane 12. The application 18 extends over the entire diameter of the membrane 12 and is aligned with the recess 16. Its width corresponds approximately to one third of the diameter. In the region of the application 18, the membrane is covered over the full surface by the contact gel, with the thickness of the gel layer being approx. 1 mm. A gel layer is not present outside the application 18.

The container 51 with the attachment 10 accommodated therein can be closed by the cover 61. The cover 61 comprises an edge region 62 which is supported on the edge 55 of the container 51 and on the upper side of the attachment 10 when it is closed. A circular shoulder 63 is arranged centrally on the inner side of the cover 61. The outer contour of said shoulder corresponds to the inner contour of the casing section 14 of the attachment 10. In the shoulder 63, in turn, an elongate recess 64 is formed which is set back from the end surface of the shoulder 63. Its extent substantially corresponds to the extent of the strip-shaped application 18 on the inner side of the membrane 12. In the packaged state, the region of the shoulder 63 outside the recess 64 makes contact with the inner side of the membrane 12 over the full surface and thus prevents the ultrasound contact gel of the application 18 from being distributed into further regions of the membrane 12. The cover 61 finally surrounds a tab 65 which adjoins the edge 62 and with which the cover 61 can be removed manually simply and rapidly.

So that precise pressure measurements can be undertaken with the pressure measuring device integrated in the ultrasound probe, said pressure measuring device should be regularly calibrated. During a first calibrating process, such a calibration is undertaken on the basis of an initial pressure which is brought about by the prestress of the membrane of the attachment according to the invention. In the calibration mode, the user is instructed to place the attachment onto the ultrasound probe and to hold the latter in a certain orientation (e.g. with the end face vertically downwards), in which case the membrane should remain free, without an external action of force. The attachments are manufactured in such a manner that a known pressure value (e.g. in the range of 3-10 mmHg) is produced in interaction with the ultrasound probe. If the value determined by the pressure measuring device in this configuration deviates from this known pressure value, a correction value can be determined from the corresponding difference. In the simplest case, it is an offset value used to correct future pressure measurements until a calibration is carried out again.

It is possible to carry out a probe-specific initial calibration, in particular by the manufacturer, with the pressure value produced by the attachments being precisely determined for the specific probe and being stored in the probe, in a control unit and/or on a server.

It is likewise possible to carry out a first pressure measurement in the calibration mode even before the attachment has been placed on. From the different pressure values before and after the attachment is placed on, further correction parameters can be determined, e.g. a correction factor which is used together with the offset in order to correct the pressure measurements.

The pressure value after the attachment is placed on (or the difference from the pressure value before same is placed on) can also be used to identify whether the attachment has been placed correctly onto the ultrasound probe. If a pressure value is too low or too high or a difference is too low or too high, a warning is output and the user is instructed to check the correct fastening of the attachment.

A further possible type of calibration is basically independent of the attachment according to the invention, but can readily also be used when the attachment is used. It is also possible to use this further approach in combination with the aforementioned calibration steps. In this case, at least two pressure values in different orientations of the ultrasound probe are determined. Correction values can then be determined from said pressure values.

For example, in the calibration mode, the user is instructed to orient the probe initially with the end face vertically upwards, after which a first measurement is carried out. Subsequently, a second measurement is undertaken with a downwardly directed end face. Since the action of the weight force acting on the masses relevant to the pressure measurement is in the opposite direction, different pressure values result. Since the masses (elements of the ultrasound probe and optionally elements of the attachment) are known, the pressure measuring device can be calibrated on the basis of the measured pressures and/or on the basis of a pressure difference.

The invention is not restricted to the exemplary embodiment illustrated. In particular, a thinner membrane material can also be used. The ring-like fastening region can be formed by an element made of a different material in which the membrane is fastened, e.g. clamped. Its geometry can be adapted to different ultrasound heads with linear or curved arrays, its shape can therefore also correspond to that of an ellipse, a rectangle or the like. In addition, the attachment can be fastened to the ultrasound head in another way, and the attachment can comprise casing-side sections or components which, when the attachment is fastened, extend further rearwards, along the handle of the ultrasound probe. The transmission of germs can thus be even more effectively prevented.

The packaging can also be designed differently. It can be manufactured in particular from a very wide variety of materials, e.g. cardboard, (bio)plastics, foamed materials, etc., or combinations of materials.

In summary, it can be determined that the invention provides an attachment which is simple to handle and permits a high signal quality.

The invention claimed is:

1. A replaceable attachment for an ultrasound probe comprising:
    a ring-like fastening region for fastening the replaceable attachment to the ultrasound probe;
    a flexible membrane arranged on the fastening region, wherein a first contact medium is applied to an inner contact surface of the flexible membrane, the inner contact surface is configured to make contact with an end face of the ultrasound probe when the replaceable attachment is fastened to the ultrasound probe, before the replaceable attachment is fastened, the first contact medium is distributed on an array region of the inner contact surface, a quantity of the first contact medium in the array region is at least twice as large as in a remaining region of the inner contact surface, a positioning and extent of the array region is configured to position a piezo array of the ultrasound probe, a casing section comprising four curved segments of identical length surrounds the flexible membrane, rounded corners are located at transitions between each curved segment, and protrusions are formed in each rounded corner that extend radially inward from each rounded corner.

2. The replaceable attachment according to claim 1, wherein the array region is covered substantially over a full area by the first contact medium, and the remaining region of the inner contact surface is substantially free from the first contact medium.

3. The replaceable attachment according to claim 1, wherein the array region is substantially rectangular.

4. The replaceable attachment according to claim 1, wherein a second contact medium is applied to an outer surface of the flexible membrane before the replaceable attachment is fastened.

5. The replaceable attachment according to claim 1, further comprising:
    a tamper-evident element having a geometry which is adapted to interact with a contact geometry of the ultrasound probe, when the replaceable attachment fastened to the ultrasound probe is being pulled off, in such a manner that the tamper-evident element is mechanically damaged.

6. The replaceable attachment according to claim 1, wherein a rectangular recess is formed between a pair of the protrusions on an inner side of the casing section and extends as far as an end of the casing section opposite the flexible membrane.

7. The replaceable attachment according to claim 1, wherein an area of the array region is at least 60% and at most 175% of an area of the piezo array.

8. An ultrasound probe with the replaceable attachment according to claim 1.

9. The ultrasound probe according to claim 8, wherein the fastening region of the replaceable attachment has a contour for interaction with a mating contour of the ultrasound probe, wherein the contour and the mating contour are designed in such a manner that the replaceable attachment is configured to be placed onto the ultrasound probe only in one or two mutually opposite orientations.

10. The ultrasound probe according to claim 8, wherein the end face has a convex geometry, and the flexible membrane of the replaceable attachment is deformed in accordance with the convex geometry as the replaceable attachment is being placed thereon.

11. The ultrasound probe according to claim 10, wherein a prestress is built up in the flexible membrane by the deformation, and the ultrasound probe comprises a pressure sensor for measuring an initial pressure exerted because of the prestress on the ultrasound probe via the replaceable attachment placed thereon.

12. A packaged attachment, comprising:
the replaceable attachment according to claim 1 and a packaging, wherein the packaging comprises a cup-like main part and a cover, wherein an internal geometry of the cup-like main part is adapted to an external geometry of the replaceable attachment such that the cup-like main part is configured to receive the replaceable attachment, and the cover has an external geometry which is adapted to an internal geometry of the replaceable attachment such that the cover is configured to be suitably inserted into the replaceable attachment when the replaceable attachment is received in the cup-like main part.

13. The packaged attachment according to claim 12, wherein the cover of the cup-like main part has a recess on an inner side which runs parallel to the flexible membrane of the replaceable attachment when the replaceable attachment is received in the packaging, the geometry of which recess is adapted to a geometry of the array region.

14. The packaged attachment according to claim 13, wherein, when the replaceable attachment is arranged between the cup-like main part and the cover, the inner contact surface of the replaceable attachment outside a region defined by the recess is contacted over the full surface in such a manner that an escape of the first contact medium out of the array region into the remaining region is impeded.

15. The packaged attachment according to claim 12, wherein a quantity of a second contact medium is contained in the cup-like main part, and therefore the outer surface of the flexible membrane of the received replaceable attachment is dipped over a large area in the second contact medium.

* * * * *